United States Patent
Lechner et al.

(10) Patent No.: US 11,471,393 B2
(45) Date of Patent: Oct. 18, 2022

(54) AGENT FOR THE TREATMENT OF KERATINOUS FIBERS CONTAINING THE REACTION PRODUCT OF TWO ORGANIC $C_1$-$C_6$ ALKOXY SILANES AND WATER

(71) Applicant: Henkel AG & Co. KGaA, Duesseldorf (DE)

(72) Inventors: Torsten Lechner, Langenfeld (DE); Juergen Schoepgens, Schwalmtal (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/436,032

(22) PCT Filed: Jan. 24, 2020

(86) PCT No.: PCT/EP2020/051822
§ 371 (c)(1),
(2) Date: Sep. 2, 2021

(87) PCT Pub. No.: WO2020/177945
PCT Pub. Date: Sep. 10, 2020

(65) Prior Publication Data
US 2022/0168202 A1   Jun. 2, 2022

(30) Foreign Application Priority Data
Mar. 6, 2019 (DE) .......................... 102019203083.1

(51) Int. Cl.
*A61Q 5/10* (2006.01)
*A61K 8/58* (2006.01)
*A61Q 5/06* (2006.01)
*A61K 8/19* (2006.01)
*A61K 8/81* (2006.01)

(52) U.S. Cl.
CPC ............... *A61K 8/585* (2013.01); *A61K 8/19* (2013.01); *A61K 8/8147* (2013.01); *A61Q 5/065* (2013.01); *A61K 2800/88* (2013.01)

(58) Field of Classification Search
CPC ...... A61Q 5/10; A61Q 5/065; A61K 2800/88; A61K 8/585; A61K 2800/432; A61K 8/89
USPC ............................................................ 8/405
See application file for complete search history.

(56) References Cited

U.S. PATENT DOCUMENTS

| | | | |
|---|---|---|---|
| 7,959,687 B2 * | 6/2011 | Charrier | A61Q 5/10 8/408 |
| 7,976,585 B2 * | 7/2011 | Cremer | C09B 69/101 8/405 |
| 8,029,577 B2 * | 10/2011 | Samain | A61K 8/585 8/581 |
| 8,343,238 B1 * | 1/2013 | Lopez | A61Q 5/10 8/408 |
| 2010/0083446 A1 * | 4/2010 | Brun | A61K 8/891 8/405 |
| 2010/0297649 A1 * | 11/2010 | Oliveira | C12Q 1/6841 435/5 |
| 2010/0303748 A1 * | 12/2010 | Hercouet | A61Q 5/10 8/405 |

FOREIGN PATENT DOCUMENTS

| | | |
|---|---|---|
| EP | 2168633 A2 | 3/2010 |
| WO | 2012038880 A2 | 3/2012 |
| WO | 2013068979 A2 | 5/2013 |

OTHER PUBLICATIONS

STIC Search Report dated Apr. 20, 2022.*

* cited by examiner

*Primary Examiner* — Eisa B Elhilo
(74) *Attorney, Agent, or Firm* — Lorenz & Kopf, LLP

(57) ABSTRACT

The subject of the present application is a cosmetic composition for the treatment of keratinous material, in particular keratinous fibers, comprising
(a) a product obtained by mixing
(a1) one or more organic $C_1$-$C_6$ alkoxy silanes of the formula (I)

$$H_2N\text{-}L\text{-}Si(OR_1)_3 \quad \text{(I)}$$

where
L is a linear or branched divalent $C_1$-$C_{20}$ alkylene group,
$R_1$ represents a $C_1$-$C_6$ alkyl group, with
(a2) one or more organic $C_1$-$C_6$ alkoxy silanes of the formula (II)

$$R_2\text{—}Si(OR_3)_3 \quad \text{(II)}$$

where
$R_2$ represents a $C_1$-$C_{12}$ alkyl group, and
$R_3$ represents a $C_1$-$C_6$ alkyl group, and
(a3) water, and,
based on the total weight of the composition
(b) one or more $C_1$-$C_6$ alcohols in a total amount of from 0.001 to 10.0% by weight; and
(c) 0.001 to 10.0% by weight of water.

20 Claims, No Drawings

AGENT FOR THE TREATMENT OF KERATINOUS FIBERS CONTAINING THE REACTION PRODUCT OF TWO ORGANIC $C_1$-$C_6$ ALKOXY SILANES AND WATER

CROSS-REFERENCE TO RELATED APPLICATION

This application is a U.S. National-Stage entry under 35 U.S.C. § 371 based on International Application No. PCT/EP2020/051822, filed Jan. 24, 2020, which was published under PCT Article 21(2) and which claims priority to German Application No. 102019203083.1, filed Mar. 6, 2019, which are all hereby incorporated in their entirety by reference.

TECHNICAL FIELD

The present application is in the field of cosmetics and concerns a cosmetic composition for the treatment of keratinous material, comprising a product (a) obtained by mixing a certain $C_1$-$C_6$ alkoxy silane (a1) of formula (I) and a certain $C_1$-$C_6$ alkoxy silane (a2) of formula (II) with water (a3). Furthermore, the composition is exemplified in that its content of $C_1$-$C_6$ alcohols (b), and water (c) is at most 10.0% by weight each.

A second object of the present disclosure is a multi-component packaging unit (kit-of-parts) for coloring keratinous material, which comprises, separately packaged in two packaging units, the cosmetic preparations (A) and (B), the preparation (A) being a preparation of the first object of the present disclosure and the preparation (B) containing at least one coloring compound.

BACKGROUND

The change in shape and color of keratin fibers, especially hair, is an important area of modern cosmetics. To change the hair color, the expert knows various coloring systems depending on coloring requirements. Oxidation dyes are usually used for permanent, intensive dyeings with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair.

EP 2168633 B1 deals with the task of producing long-lasting hair colorations using pigments. The paper teaches that when a combination of pigment, organic silicon compound, hydrophobic polymer and a solvent is used on hair, it is possible to produce colorations that are particularly resistant to shampooing.

The organic silicon compounds used in EP 2168633 B1 are reactive compounds from the class of alkoxy silanes. These alkoxy silanes hydrolyze at high rates in the presence of water and form hydrolysis products and/or condensation products, depending on the amounts of alkoxy silane and water used in each case. The influence of the amount of water used in this reaction on the properties of the hydrolysis or condensation product are described, for example, in WO 2013068979 A2.

When these hydrolysis or condensation products are applied to keratinous material, a film or coating is formed on the keratinous material, which completely envelops the keratinous material and, in this way, strongly influences the properties of the keratinous material. Possible areas of application include permanent styling or permanent shape modification of keratin fibers. In this process, the keratin fibers are mechanically shaped into the desired form and then fixed in this form by forming the coating described above. Another particularly suitable application is the coloring of keratin material; in this application, the coating or film is produced in the presence of a coloring compound, for example a pigment. The film colored by the pigment remains on the keratin material or keratin fibers and results in surprisingly wash-resistant colorations.

The great advantage of the alkoxy silane-based dyeing principle is that the high reactivity of this class of compounds enables fast coating. This means that extremely good coloring results can be achieved after short application periods of just a few minutes. In addition to these advantages, however, the high reactivity of alkoxy silanes also has some disadvantages. Thus, even minor changes in production and application conditions, such as changes in humidity and/or temperature, can lead to sharp fluctuations in product performance. Most importantly, the work leading to this disclosure has shown that the alkoxy silanes are extremely sensitive to the conditions encountered in the manufacture of the keratin treatment agents. If these manufacturing conditions deviate only slightly from their optimal range of values, this can lead to partial or even complete loss of product performance. In particular, the dyeing performance of an alkoxy silane-based dyeing agent produced under less-than-optimal conditions can drop dramatically. It has been found that the content of $C_1$-$C_6$ alcohols and water in the keratin treatment or coloring agent has a major influence on the product performance.

BRIEF SUMMARY

Cosmetic compositions and multicomponent packaging units including the cosmetic compositions for treating keratinous materials are provided. In an exemplary embodiment, a cosmetic composition for treating keratinous material is produced from a product made by mixing an organic $C_1$-$C_6$ alkoxy silane of formula (I), another organic $C_1$-$C_6$ alkoxy silane of formula (II), and water. Formula (I) is $H_2N$-L-Si$(OR_1)_3$, and Formula (II) is $R_2$—Si$(OR_3)_3$, where L is a $C_1$-$C_{20}$ alkylene group, $R_1$ and $R_3$ independently represent one or more $C_1$-$C_6$ alkyl groups, and $R_2$ represents a $C_{1-12}$ alkyl group. The cosmetic composition includes a $C_1$-$C_6$ alcohol at from about 0.001 to about 10 weight percent, and the water at from about 0.001 to about 10 weight percent, based on a total weight of the cosmetic composition.

A multicomponent packaging unit (a kit-of-parts) for dyeing keratinous material is provided in another embodiment. The kit of parts includes a first packaging unit containing a preparation (A) and a second packaging unit containing a preparation (B). Preparation A is made from a product produced by mixing an organic $C_1$-$C_6$ alkoxy silane of formula (I), another organic $C_1$-$C_6$ alkoxy silane of formula (II), and water. Formula (I) is $H_2N$-L-Si(OR$_1$)$_3$, and Formula (II) is $R_2$—Si(OR$_3$)$_3$, where L is a $C_1$-$C_{20}$ alkylene group, $R_1$ and $R_3$ independently represent one or more $C_1$-$C_6$ alkyl groups, and $R_2$ represents a $C_{1-12}$ alkyl group. The preparation (A) includes a $C_1$-$C_6$ alcohol at from about 0.001 to about 10 weight percent, and the water at from about 0.001 to about 10 weight percent, based on a total weight of the preparation (A). Preparation (B) includes a colorant compound selected from the group of pigments and/or direct dyes.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was the task of the present application to find a preparation for the treatment of keratin material which contains the reactive alkoxy silanes in an optimum mixture and composition. The aim was to hydrolyze and condense the alkoxy silanes used to prepare the agent in a targeted manner so that compositions with optimum application properties could be obtained. In particular, the agents prepared by this method should have improved dyeing performance, i.e., when used in a dyeing process, dyeing's with higher color intensity and improved fastness properties, especially improved wash fastness and improved rub fastness, should be obtained.

Surprisingly, it has now been found that the task can be excellently solved if the composition for treating the keratin material is prepared by mixing two silanes of certain structural formulae (I) and (II) with water, all three reactants (i.e., the silanes of formulae (I) and (II) and the water) preferably being reacted with one another in certain molar ratios. Furthermore, it is essential for the composition that the alcohols released during the reaction of the alkoxy silanes are removed as completely as possible from the reaction mixture. It has also been found to be essential that the water content in the preparation should not exceed a certain maximum amount.

A first object of the present disclosure is a cosmetic composition for treating keratinous material, in particular keratinous fibers, comprising:
(a) a product obtained by mixing
(a1) one or more organic $C_1$-$C_6$ alkoxy silanes of the formula (I)

$$H_2N\text{-L-Si}(OR_1)_3 \qquad (I)$$

where
L is a linear or branched divalent $C_1$-$C_{20}$ alkylene group,
$R_1$ represents a $C_1$-$C_6$ alkyl group, with
(a2) one or more organic $C_1$-$C_6$ alkoxy silanes of the formula (II)

$$R_2\text{—Si}(OR_3)_3 \qquad (II)$$

where
$R_2$ represents a $C_1$-$C_{12}$ alkyl group, and
$R_3$ represents a $C_1$-$C_6$ alkyl group, and
(a3) water, and,
based on the total weight of the composition
(b) one or more $C_1$-$C_6$ alcohols in a total amount of from about 0.001 to about 10.0% by weight; and
(c) about 0.001 to about 10.0% by weight of water.

It has been shown that hair treatment agents with the above composition, when used in a dyeing process, resulted in very intense and uniform colorations with particularly good rub fastness and wash fastness.

Agent for the Treatment of Keratinous Material

Keratinous material includes hair, skin, and nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

Techniques for treating keratinous material are understood to mean, for example, techniques for coloring the keratinous material, techniques for reshaping or shaping keratinous material, keratinous fibers, or also techniques for conditioning or caring for the keratinous material. The agents produced by the process of the present disclosure are particularly suitable for coloring keratinous material, for coloring keratinous fibers, which are preferably human hair.

The term "coloring agent" is used in the context of the present disclosure to refer to a coloring of the keratin material, of the hair, caused using coloring compounds, such as thermochromic and photochromic dyes, pigments, mica, direct dyes and/or oxidation dyes. In this staining process, the colorant compounds are deposited in a particularly homogeneous and smooth film on the surface of the keratin material or diffuse into the keratin fiber. The film forms in situ by oligomerization or polymerization of the organic silicon compound(s), and by the interaction of the color-imparting compound and organic silicon compound and optionally other ingredients, such as a film-forming hydrophilic polymer.

Product of $C_1$-$C_6$ Alkoxy Silanes (a1) with $C_1$-$C_6$ Alkoxy Silanes (a2) and Water (a3)

As the first ingredient (a) essential to the present disclosure, the composition as contemplated herein contains a product obtained by mixing a $C_1$-$C_6$ alkoxy silane (a1) of formula (I) with a $C_1$-$C_6$ alkoxy silane (a2) of formula (II) and water (a3).

The $C_1$-$C_6$ alkoxy silanes of formulae (I) and (II) are each highly reactive compounds that undergo a hydrolysis reaction in the presence of water. This hydrolysis reaction is exothermic and starts when silanes (I) or (II) meet water.

The organic $C_1$-$C_6$ alkoxy silane(s) are organic, non-polymeric silicon compounds, preferably selected from the group of silanes containing one, two or three silicon atoms.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds of the present disclosure are preferably compounds containing one to three silicon atoms. Organic silicon compounds preferably contain one or two silicon atoms.

According to IUPAC rules, the term silane chemical compounds is based on a silicon skeleton and hydrogen. In organic silanes, the hydrogen atoms are completely or partially replaced by organic groups such as (substituted) alkyl groups and/or alkoxy groups.

A characteristic feature of the $C_1$-$C_6$ alkoxy silanes as contemplated herein is that three $C_1$-$C_6$ alkoxy groups are directly bonded to the silicon atom. The $C_1$-$C_6$-alkoxy silanes of the present disclosure thus comprise at least one structural unit R'Si—(O—$C_1$-$C_6$-alkyl)$_3$, the radical R' in each case representing the corresponding structural unit in the $C_1$-$C_6$-alkoxy silanes of the formulae (I) and (II).

These $C_1$-$C_6$ alkoxy groups bonded to the silicon atom are very reactive and are hydrolyzed at high rates in the presence of water, the reaction rate depending, among other things, on the number of hydrolysable groups per molecule. If the hydrolysable $C_1$-$C_6$ alkoxy group is an ethoxy group, the organic silicon compound preferably contains a structural unit R'Si(O—$CH_2$—$CH_3$)$_3$. The R' residue here again exemplifies the fourth structural unit bonded to the silicon atom.

In the case of the $C_1$-$C_6$ alkoxy silanes (a1) of the formula (I)

$$H_2N\text{-}L\text{-}Si(OR_1)_3 \text{ is}$$ (I)

L is a linear or branched divalent $C_1$-$C_{20}$ alkylene group, and $R_1$ represents a $C_1$-$C_6$ alkyl group.

The substituents $R_1$, $R_2$, $R_3$ and L in the compounds of formula (I) and (II) are exemplified below:

Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—) and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—$CH(CH_3)$—) and (—$CH_2$—$CH(CH_3)$—$CH_2$—).

In the middle part of the organic silicon compound of formula (I) is the structural unit or linker -L- which represents a linear or branched divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each—L grouping may form—two bonds.

Preferably -L- stands for a linear, divalent $C_1$-$C_{20}$ alkylene group. Further preferably -L- stands for a linear divalent $C_1$-$C_6$ alkylene group. Particularly preferred -L stands for a methylene group (—$CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). Very preferably L stands for a propylene group (—$CH_2$—$CH_2$—$CH_2$—)

The organic silicon compounds of formula (I)

$$H_2N\text{-}L\text{-}Si(OR_1)_3 \tag{I}$$

carry the silicon-containing grouping —Si(OR$_1$)$_3$ at one end.

Here $R_1$ stands for a $C_1$-$C_6$ alkyl group. Particularly preferably, $R_1$ represents a methyl group or an ethyl group.

Hair treatment compositions with particularly good properties could be prepared when, to obtain product (a), at least one organic $C_1$-$C_6$ alkoxy silane (a1) of formula (I) was reacted with a $C_1$-$C_6$ alkoxy silane (a2) of formula (II) and water, in which $R_1$ represents a methyl group or an ethyl group.

Particularly suitable organic $C_1$-$C_6$ alkoxy silanes (a1) of the formula (I) for solving the problem as contemplated herein are (3-Aminopropyl)triethoxysilane

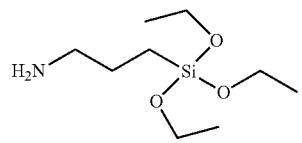

(3-Aminopropyl)trimethoxysilane

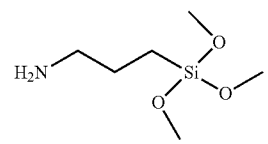

(2-Aminoethyl)triethoxysilane

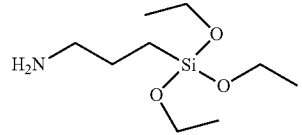

(2-Aminoethyl)trimethoxysilane

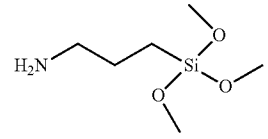

(3-Dimethylaminopropyl)triethoxysilane

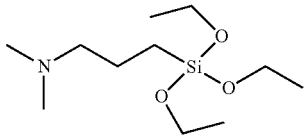 [SMILES: CCO[Si](CCCN(C)C)(OCC)OCC]

(3-Dimethylaminopropyl)trimethoxysilane

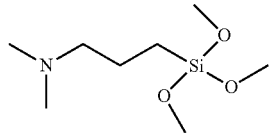

(2-Dimethylaminoethyl)triethoxysilane

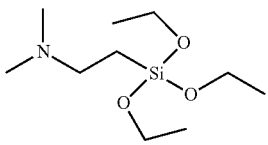

(2-Dimethylaminoethyl)trimethoxysilane and/or

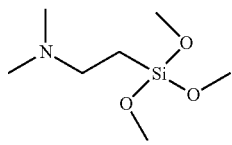

In a further preferred embodiment, a composition as contemplated herein is exemplified in that it utilized a product (a) obtained by mixing (a1) one or more organic $C_1$-$C_6$ alkoxy silanes of the formula (I) from the group of (3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-Dimethylaminoethyl)triethoxysilane and/or
(2-Dimethylaminoethyl)trimethoxysilane.

The organic silicon compounds of formula (I) are commercially available.

(3-aminopropyl)trimethoxysilane, for example, can be purchased from Sigma-Aldrich®. Also (3-aminopropyl)triethoxysilane is commercially available from Sigma-Aldrich®.

In the case of the $C_1$-$C_6$ alkoxy silanes (a2) of the formula (II)

$$R_2\text{—Si}(OR_3)_3 \quad (II)$$

(I)

$R_2$ represents a $C_1$-$C_{12}$ alkyl group, and $R_3$ represents a $C_1$-$C_6$ alkyl group.

In the organic $C_1$-$C_6$ alkoxy silanes of formula (II), the $R_2$ radical represents a $C_1$-$C_{12}$ alkyl group. This $C_1$-$C_{12}$ alkyl group is saturated and can be linear or branched. Preferably, $R_2$ represents a linear $C_1$-$C_8$ alkyl group. Preferably $R_2$ stands for a methyl group, an ethyl group, an n-propyl group, an n-butyl group, an n-pentyl group, an n-hexyl group, an n-octyl group or an n-dodecyl group. Particularly preferably, $R_2$ represents a methyl group, an ethyl group, an n-hexyl group or an n-octyl group.

In the organic silicon compounds of formula (II), the radical $R_3$ represents a $C_1$-$C_6$ alkyl group. Particularly preferably, $R_3$ represents a methyl group or an ethyl group.

Organic silicon compounds of the formula (II) which are particularly suitable for solving the problem as contemplated herein are Methyltrimethoxysilane

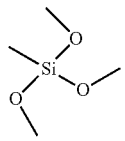

Methyltriethoxysilane

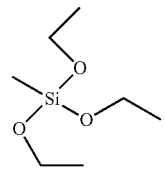

Ethyltrimethoxysilane

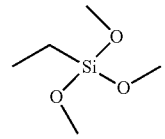

Ethyltriethoxysilane

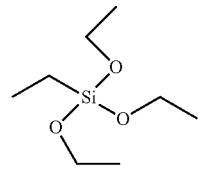

n-Propyltrimethoxysilane (also referred to as propyltrimethoxysilane)

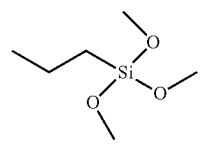

n-Propyltriethoxysilane (also referred to as propyltriethoxysilane)

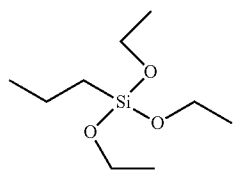

n-Hexyltrimethoxysilane (also referred to as hexyltrimethoxysilane)

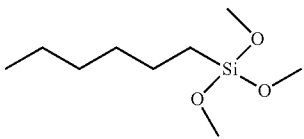

n-Hexyltriethoxysilane (also referred to as hexyltriethoxysilane)

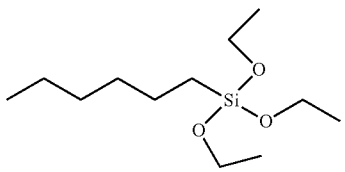 [SMILES: CCCCCC[Si](OCC)(OCC)OCC]

n-Octyltrimethoxysilane (also known as octyltrimethoxysilane)

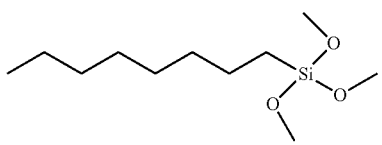

n-Octyltriethoxysilane (also known as octyltriethoxysilane)

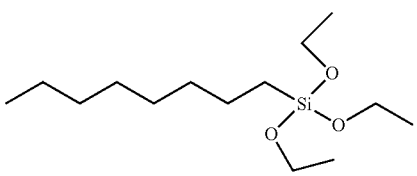 [SMILES: CCCCCCCC[Si](OCC)(OCC)OCC]

n-Dodecyltrimethoxysilane (also referred to as dodecyltrimethoxysilane) and/or

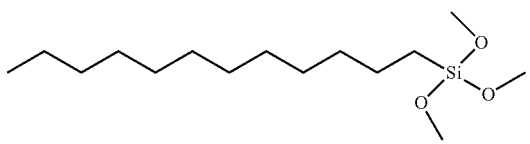 [SMILES: CCCCCCCCCCCC[Si](OC)(OC)OC]

n-Dodecyltriethoxysilanes (also known as dodecyltriethoxysilane)

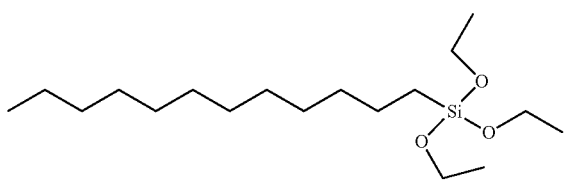 [SMILES: CCCCCCCCCCCC[Si](OCC)(OCC)OCC]

In a further preferred embodiment, a composition as contemplated herein is exemplified in that it comprises a product (a) obtained by mixing (a2) one or more organic $C_1$-$C_6$ alkoxy silanes of the formula (II) selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane and/or
Dodecyltriethoxysilane,
and made to react with water.

When specific $C_1$-$C_6$ alkoxy silanes of formula (I) and (II) were mixed with water, a product (a) with very particularly advantageous properties was obtained.

In the context of one embodiment, very particularly preferred is a cosmetic composition for treating keratinous material, in particular keratinous fibers, comprising
(a) a product obtained by mixing
(a1) (3-Aminopropyl)triethoxysilane with
(a2) Methyltrimethoxysilane and
(a3) Water.

In the context of one embodiment, very particularly preferred is a cosmetic composition for treating keratinous material, in particular keratinous fibers, comprising
(a) a product obtained by mixing
(a1) (3-Aminopropyl)triethoxysilane with
(a2) ethyltriethoxysilane and
(a3) Water.

In the context of one embodiment, very particularly preferred is a cosmetic composition for treating keratinous material, in particular keratinous fibers, comprising
(a) a product obtained by mixing
(a1) (3-Aminopropyl)triethoxysilane with
(a2) Methyltriethoxysilane and
(a3) Water.

In the context of one embodiment, very particularly preferred is a cosmetic composition for treating keratinous material, in particular keratinous fibers, comprising
(a) a product obtained by mixing
(a1) (3-Aminopropyl)triethoxysilane with
(a2) Propyltriethoxysilane and
(a3) Water.

In the context of one embodiment, very particularly preferred is a cosmetic composition for treating keratinous material, in particular keratinous fibers, comprising
(a) a product obtained by mixing
(a1) (3-Aminopropyl)triethoxysilane with
(a2) Hexyltriethoxysilane and
(a3) Water.

In the context of one embodiment, very particularly preferred is a cosmetic composition for treating keratinous material, in particular keratinous fibers, comprising
(a) a product obtained by mixing
(a1) (3-Aminopropyl)triethoxysilane with
(a2) Octyltriethoxysilane and
(a3) Water.

Since both silanes of the structural groups (a1) and (a2) can each react with water during hydrolysis and with each other during a later condensation, the reactions leading to product (a) are complex, and mixtures of monomeric and oligomeric silane condensates are formed with the mixing. It is believed that when (a1) is mixed with (a2) and (a3), the following reactions are initiated:

Hydrolysis of $C_1$-$C_6$ alkoxy silane of formula (I) with water (reaction scheme using 3-aminopropyltriethoxysilane as an example):

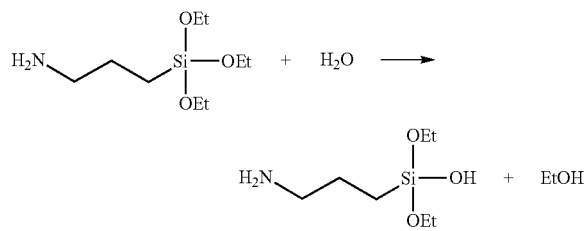

Depending on the amount of water (a3) used, the hydrolysis reaction can also take place several times per $C_1$-$C_6$ alkoxy silane (a1) used:

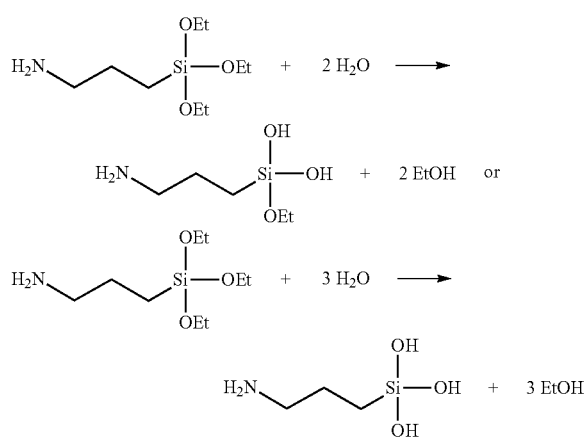

Hydrolysis of $C_1$-$C_6$ alkoxy silane of formula (II) with water (reaction scheme using methyltrimethoxysilane as an example):

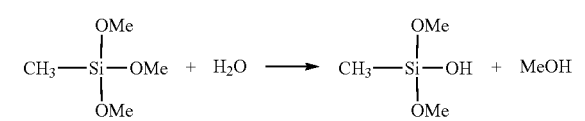

Depending on the amount of water (a3) used, the hydrolysis reaction can also take place several times per $C_1$-$C_6$ alkoxy silane (a2) used:

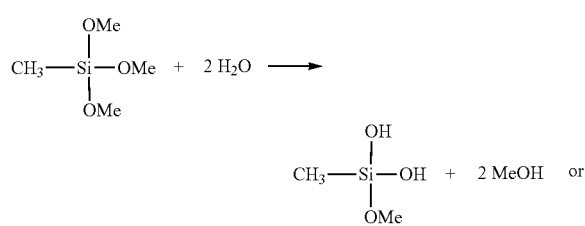

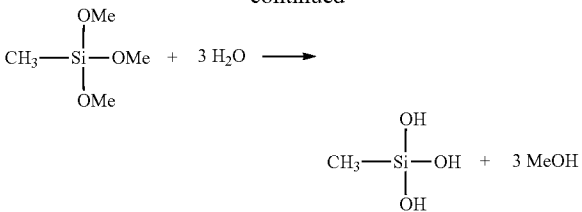

Since the hydrolysis reaction is exothermic, it has been found to be particularly advantageous to stir or mix the reaction mixture of the $C_1$-$C_6$ alkoxy silanes (a1) and (a2) and water (a3) for improved heat dissipation.

The reaction of the organic $C_1$-$C_6$ alkoxy silanes (a1) and (a2) with water (a3) leading to the product (a) can take place in different ways. One possibility is to introduce the desired amount of water (a3) into the reaction vessel or reactor and then add the $C_1$-$C_6$ alkoxy silane(s) (a1) and (a2).

In another embodiment, the appropriate amounts of $C_1$-$C_6$ alkoxy silanes (a1) are first mixed with the $C_1$-$C_6$ alkoxy silanes (a2) in a reaction vessel or reactor, and then the desired amount of water (a3) is added.

The water can be added continuously, in partial quantities or directly as a total quantity. To ensure the required temperature control, the reaction mixture is preferably cooled and/or the amount and rate of water added is adjusted. To maintain the desired temperature ranges, it has been found to be particularly suitable to add the necessary amount of water continuously dropwise to a mixture of silanes of formulae (I) and (II).

Depending on the amount of silanes used, the addition and reaction can take place over a period of about 2 minutes to about 72 hours.

Due to the high reactivity of the $C_1$-$C_6$ alkoxy silanes (a1) and (a2), complex mixtures of hydrolyzed and condensed silanes, respectively, can be formed when they react with water (a3). The exact composition of these mixtures is determined primarily by the molar amounts in which components (a1), (a2) and (a3) are each used in the reaction leading to product (a).

The work leading to the present disclosure has shown that when the composition as contemplated herein was applied to the keratin material, a stable and resistant coating could be produced when the $C_1$-$C_6$ alkoxy silanes (a1) and (a2) and water (a3) were mixed in certain molar ratios and consequently also reacted with each other in certain molar ratios.

It has been found to be particularly preferable to use the organic $C_1$-$C_6$ alkoxy silanes (a2) in a molar excess compared with the organic $C_1$-$C_6$ alkoxy silanes (a1). Very preferably, the silanes (a2) and (a1) are mixed in a molar ratio (a2)/(a1) of from about 3.0 to about 8.0, preferably from about 3.5 to about 7.5, more preferably from about 4.0 to about 7.0, still more preferably from about 4.5 to about 6.5, and most preferably from about 5.4 to about 5.9.

By maintaining these molar ratios (a2)/(a1) in the reaction leading to product (a), it was possible to ensure that a silane condensate was obtained which contained the amino alkyl groups (i.e., the structural units -L-NH2 derived from the silanes of formula (I)) at an optimum distance from one another. In this context, it is assumed that the amino alkyl groups in the silane condensate act as linkers through which adhesion to the keratinous material is achieved. If the silane condensate contains too few of these linker units, there is a risk that the silane coating will not adhere optimally to the keratin material when the preparation as contemplated herein is used. However, if too many of these linker units are present in the silane condensate, this seems to create such a bulky molecular geometry that adhesion between the silane coati-ng and the keratin material is not optimal in this case either.

Example

| (a1) | (3-Aminopropyl)triethoxysilane | molar mass = 221.37 g/mol |
| --- | --- | --- |
| (a2) | Methyltrimethoxysilane | Molar mass = 136.22 g/mol |

266.6 g of (3-aminopropyl)triethoxysilane (1.204 mol) was placed in a reaction vessel. With stirring, 933.4 g of methyltrimethoxysilane (6.852 mol) was added at room temperature.

The molar ratio (a2)/(a1) is (6.852 mol)/(1.204 mol)=5.69

Example

| (a1) | (3-Aminopropyl)triethoxysilane | molar mass = 221.37 g/mol |
| --- | --- | --- |
| (a2) | Methyltrimethoxysilane | Molar mass = 136.22 g/mol |
| (a2) | Ethyltriethoxysilane | molar mass = 192.33 g/mol |

266.6 g of (3-aminopropyl)triethoxysilane (1.204 mol) was placed in a reaction vessel. With stirring, 466.6 g of methyltrimethoxysilane (3.426 mol) and 658.922 g (3.426 mol) of ethyltriethoxysilane were added at room temperature.

The molar ratio $(a2)/(a1)$ is (3.426 mol+3.426 mol)/(1.204 mol)=5.69

In the context of another very particularly preferred embodiment, a cosmetic composition for treating keratinous material is exemplified in that the organic $C_1$-$C_6$ alkoxy silanes (a1) and the organic $C_1$-$C_6$ alkoxy silanes (a2) are mixed with one another to give the product (a) in a molar ratio (a2)/(a1) of from about 3.0 to about 8.0, preferably from about 3.5 to about 7.5, more preferably from about 4.0 to about 7.0, still more preferably from about 4.5 to about 6.5 and very particularly preferably from about 5.4 to about 5.9.

Here, the organic $C_1$-$C_6$ alkoxy silanes (a1) are the organic $C_1$-$C_6$ alkoxy silanes of the formula (I). The organic $C_1$-$C_6$ alkoxy silanes (a2) are the organic $C_1$-$C_6$ alkoxy silanes of formula (II).

To produce agents which produce a particularly good coating on the keratin material, it has been found to be explicitly quite preferred to use water (a3) in a sub stoichiometric amount to produce product (a). In this case, the amount of water used is below the amount that would theoretically be required to hydrolyze all the hydrolysable $C_1$-$C_6$ alkoxy groups present on the Si atoms, i.e., the alkoxysilane groups. Partial hydrolysis of the organic $C_1$-$C_6$ alkoxy silanes is therefore particularly preferred.

The $C_1$-$C_6$ alkoxy silanes (a1) and water (a3) are also preferentially reacted together in certain molar ratios. The best results were obtained when the organic $C_1$-$C_6$ alkoxy silanes (a1) and water (a3) were mixed to obtain the product (a) in a molar ratio (a3)/(a1) of from about 4.0 to about 9.5, preferably from about 4.5 to about 9.0, more preferably from about 5.0 to about 8.5, still more preferably from about 5.5 to about 8.0, and most preferably from about 5.8 to about 6.4. When these molar ratios are maintained, water (a3) is used quite particularly in a about 5.8 to about 6.4-fold molar excess compared to the $C_1$-$C_6$ alkoxy silanes (a1).

Example

| (a1) | (3-Aminopropyl)triethoxysilane | molar mass = 221.37 g/mol |
| --- | --- | --- |
| (a3) | Water | molar mass = 18.02 g/mol |

266.6 g of (3-aminopropyl)triethoxysilane (1.204 mol) was placed in a reaction vessel. With stirring, 933.4 g of methyltrimethoxysilane (6.852 mol) was added at room temperature. Subsequently, 133.4 g of water (7.403 mol) was added slowly with stirring.

The molar ratio $(a3)/(a1)$ is (7.403 mol)/(1.204 mol)=6.15

In the context of another very particularly preferred embodiment, a cosmetic composition for treating keratinous material is exemplified in that the organic $C_1$-$C_6$ alkoxy silanes (a1) and water (a3) are mixed with each other to obtain the product (a) in a molar ratio (a3)/(a1) of from about 4.0 to about 9.5, preferably from about 4.5 to about 9.0, more preferably from about 5.0 to about 8.5, still more preferably from about 5.5 to about 8.0 and most preferably from about 5.8 to about 6.4.

Here, the organic $C_1$-$C_6$ alkoxy silanes (a1) are the organic $C_1$-$C_6$ alkoxy silanes of the formula (I) described above.

The $C_1$-$C_6$ alkoxy silanes (a2) and water (a3) are also preferentially reacted together in certain molar ratios. The best results were obtained when the organic $C_1$-$C_6$ alkoxy silanes (a2) and water (a3) were mixed to obtain the product (a) in a molar ratio (a3)/(a2) of from about 0.1 to about 3.5, preferably from about 0.3 to about 3.0, more preferably from about 0.5 to about 2.5, still more preferably from about 0.7 to about 2.0, and most preferably from about 0.9 to about 1.3.

When these molar ratios are maintained, water (a3) is used quite particularly in approximately equimolar amounts compared to the $C_1$-$C_6$ alkoxy silanes (a1).

Example

| (a1) | (3-Aminopropyl)triethoxysilane | molar mass = 221.37 g/mol |
| --- | --- | --- |
| (a2) | Methyltrimethoxysilane | Molar mass = 136.22 g/mol |
| (a3) | Water | molar mass = 18.02 g/mol |

266.6 g of (3-aminopropyl)triethoxysilane (1.204 mol) was placed in a reaction vessel. With stirring, 933.4 g of methyltrimethoxysilane (6.852 mol) was added at room temperature. Subsequently, 133.4 g of water (7.403 mol) was added slowly with stirring.

The molar ratio $(a3)/(a2)$ is (7.402 mol)/(6.852 mol)=1.08

(3-Aminopropyl)triethoxysilane has 3 hydrolysable ethoxy groups per silane molecule. Methyltrimethoxysilane has 3 hydrolysable methoxy groups per silane molecule.

Sum of hydrolysable $C_1$-$C_6$ alkoxy groups=[(1.204 mol)× 3]+[(6.852 mol)×3]=24.168 mol. Addition of 133.4 g water (7.403 mol) hydrolyzed 30.6% (just under one-third) of the $C_1$-$C_6$ alkoxy groups present in the silanes.

In another particularly preferred embodiment, a cosmetic composition for treating keratinous material is exemplified in that the $C_1$-$C_6$ organic alkoxy silanes (a2) and (a3) water are mixed with each other to obtain the product (a) in a molar ratio (a3)/(a2) of about 0.1 to about 3.5, preferably from about 0.3 to about 3.0, more preferably from about 0.5 to about 2.5, still more preferably from about 0.7 to about 2.0 and most preferably from about 0.9 to about 1.3.

Here, the organic $C_1$-$C_6$ alkoxy silanes (a2) are the organic $C_1$-$C_6$ alkoxy silanes of the formula (II) described above.

The preparation of product (a) from the organic $C_1$-$C_6$ alkoxy silanes (a1) with the organic $C_1$-$C_6$ alkoxy silanes (a2) and water (a3) can be carried out, for example, in a reaction vessel or a reactor, preferably in a double-walled reactor, a reactor with an external heat exchanger, a tubular reactor, a reactor with a thin-film evaporator, a reactor with a falling-film evaporator and/or a reactor with an attached condenser.

A reaction vessel that is very suitable for smaller preparations is, for example, a glass flask commonly used for chemical reactions with a capacity of 1 liter, 3 liters or 5 liters, such as a 3-liter single-neck or multi-neck flask with ground joints.

A reactor is a confined space (container, vessel) that has been specially designed and manufactured to allow certain reactions to take place and be controlled under defined conditions.

For larger approaches, it has proven advantageous to carry out the reaction in reactors made of metal. Typical reactors may include, for example, a 10-liter, 20-liter, or 50-liter capacity. Larger reactors for the production area can also include fill volumes of 100-liters, 500-liters, or 1000-liters.

Double-wall reactors have two reactor shells or reactor walls, with a tempering fluid circulating in the area between the two walls. This enables particularly good adjustment of the temperature to the required values.

The use of reactors, in particular double-walled reactors with an enlarged heat exchange surface, has also proven to be particularly suitable, whereby the heat exchange can take place either through internal installations or using an external heat exchanger.

Corresponding reactors are, for example, laboratory reactors from the company IKA®. In this context, the models "LR-2.ST" or the model "magic plant" can be mentioned.

Other reactors that can be used are reactors with thin-film evaporators, since this allows particularly good heat dissipation and thus particularly precise temperature control. Thin film evaporators are alternatively referred to as thin film evaporators. Thin film evaporators can be purchased commercially from Asahi Glassplant® Inc. for example.

In reactors with falling film evaporators, evaporation generally takes place in a tube, i.e., the liquid to be evaporated (i.e., in this case, the $C_1$-$C_6$ alcohols to be removed in step (2)) flow as a continuous liquid film. Reactors with falling film evaporators are also commercially available from various suppliers.

To produce particularly high-performance keratin treatment agents, the maintenance of specific temperature ranges has proven to be particularly advantageous in the manufacture of product (a).

In this context, it was found that a minimum temperature of about 20° C. in step (1) is particularly well suited to allow the hydrolysis to proceed at a sufficiently high rate and to ensure efficient reaction control.

On the other hand, however, heating of the reaction mixture to temperatures above about 70° C. should preferably be avoided. If the production is carried out at too high temperatures, an undesirable or excessive polymerization or condensation reaction will probably take place at this point, resulting in the inability to form a film adhering to the keratin material during subsequent application of the agent. When using an agent produced at too high temperatures in a dyeing process, it was therefore no longer possible to achieve sufficiently high color intensities.

For these reasons, the reaction or mixing of the organic $C_1$-$C_6$ alkoxy silanes (a1) with the organic $C_1$-$C_6$ alkoxy silanes (a2) and water (a3) is preferably carried out at a temperature of about 20 to about 70° C.

The temperature range given here refers to the temperature to which the mixture of $C_1$-$C_6$ alkoxy silanes (a1) and (a2) and water (a3) should be adjusted. This temperature can be measured, for example, by a calibrated thermometer protruding into this mixture. Preferably, the reaction of one or more organic $C_1$-$C_6$ alkoxy silanes with water occurs at a temperature of from about 20° C. to about 70° C., preferably from about 20 to about 65° C., more preferably from about 20 to about 60° C., still more preferably from about 20 to about 55° C., still more preferably from about 20 to about 50° C., and most preferably from about 20 to about 45° C.

In a further embodiment, a particularly preferred cosmetic composition for treating keratinous material, in particular keratinous fibers, is one containing
(a) a product obtained by mixing
(a1) one or more organic $C_1$-$C_6$ alkoxy silanes of the formula (I)

$$H_2N\text{-}L\text{-}Si(OR_1)_3 \qquad (I)$$

where
L is a linear or branched divalent $C_1$-$C_{20}$ alkylene group,
$R_1$ represents a $C_1$-$C_6$ alkyl group,
with
(a2) one or more organic $C_1$-$C_6$ alkoxy silanes of the formula (II)

$$R_2\text{—}Si(OR_3)_3 \qquad (II)$$

where
$R_2$ represents a $C_1$-$C_{12}$ alkyl group, and
$R_3$ represents a $C_1$-$C_6$ alkyl group, and
(a3) Water,
at a temperature of from about 20° C. to about 70° C., preferably from about 20 to about 65° C., further preferably from about 20 to about 60° C., still further preferably from about 20 to about 55° C., still further preferably from about 20 to about 50° C. and very particularly preferably from about 20 to about 45° C.

Adjustment of the preferred and particularly preferred temperature ranges can be accomplished by tempering the reaction vessel or reactor. For example, the reaction vessel or reactor may be surrounded from the outside by a temperature control bath, which may be a water bath or silicone oil bath, for example.

If the reaction is carried out in a double-walled reactor, a temperature-controlled liquid can also be passed through the space formed by the two walls surrounding the reaction chamber.

It may be further preferred that there is no active heating of the reaction mixture and that any increase in temperature above ambient is caused only by the exotherm of the hydrolysis. If the exothermic reaction process heats the reaction mixture strongly, cooling is again required.

The reaction of the organic $C_1$-$C_6$ alkoxy silanes with water preferably takes place at normal pressure, i.e., at a pressure of about 1013 mbar (1013 hPa).

The compositions as contemplated herein may contain the product (a) in various proportions. The specialist determines this depending on the desired thickness of the silane coating on the keratin material.

Particularly storage-stable compositions could be obtained if the composition contains—based on its total weight—one or more products (a) in a total amount of from about 30.0 to about 85.0% by weight, preferably from about 35.0 to about 80.0% by weight, more preferably from about 40.0 to about 75.0% by weight, still more preferably from about 45.0 to about 70.0% by weight and most preferably from about 50.0 to about 65.0% by weight.

In a further embodiment, very particularly preferred is a cosmetic composition for the treatment of keratinous material, comprising—based on the total weight of the composition—one or more products (a) in a total amount of from about 30.0 to about 85.0% by weight, preferably from about 35.0 to about 80.0% by weight, more preferably from about 40.0 to about 75.0% by weight, still more preferably from about 45.0 to about 70.0% by weight and very particularly preferably from about 50.0 to about 65.0% by weight.

Content of $C_1$-$C_6$ Alcohols (b) in the Composition

As described previously, mixing the reactive $C_1$-$C_6$ alkoxy silanes (a1) and (a2) with water (a3) initiates a hydrolysis reaction in which the $C_1$-$C_6$ alkoxy groups located directly on the silicon atom are hydrolyzed and the corresponding $C_1$-$C_6$ alcohols are released.

The partially or completely hydrolyzed silanes formed during hydrolysis are also reactive compounds that can undergo subsequent reactions in which these silanes of different degrees of hydrolysis condense with each other.

It is believed that the following condensation reactions, among others, may occur (possible condensation reactions shown using the mixture of (3-aminopropyl)triethoxysilane and methyltrimethoxysilane):

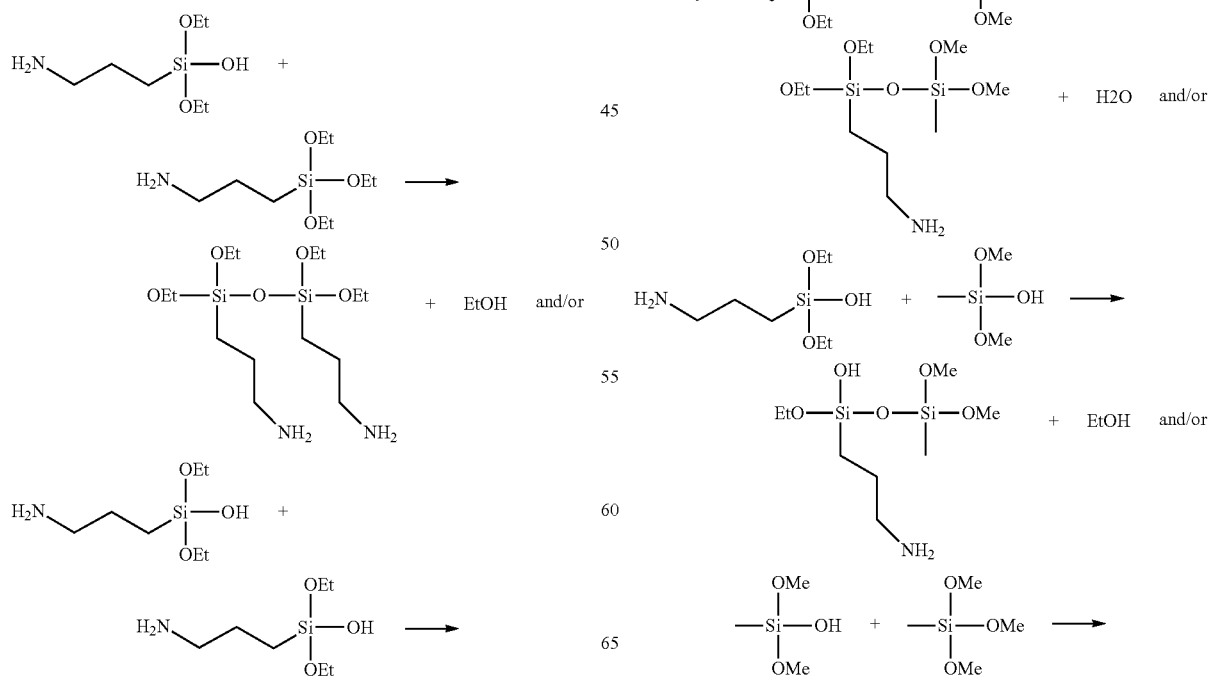

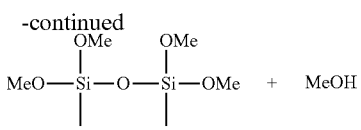

In the above exemplary reaction schemes the condensation to a dimer is shown in each case, but the more advanced condensations to oligomers with several silane atoms are also possible and preferred.

Both partially hydrolyzed and fully hydrolyzed $C_1$-$C_6$ alkoxysilanes (a1) can participate in these condensation reactions, which undergo condensation with not yet reacted, partially or also fully hydrolyzed $C_1$-$C_6$ alkoxysilanes (a1). In this case, the $C_1$-$C_6$ alkoxysilanes of type (a1) react with themselves.

Furthermore, partially hydrolyzed as well as fully hydrolyzed $C_1$-$C_6$ alkoxysilanes (a2) can also participate in the condensation reactions, which undergo condensation with not yet reacted, partially or also fully hydrolyzed $C_1$-$C_6$ alkoxysilanes (a1). In this case, the $C_1$-$C_6$ alkoxysilanes of type (a1) react the $C_1$-$C_6$ alkoxysilanes of type (a2).

Furthermore, partially hydrolyzed as well as fully hydrolyzed $C_1$-$C_6$ alkoxysilanes (a2) can also participate in the condensation reactions, which undergo condensation with not yet reacted, partially or also fully hydrolyzed $C_1$-$C_6$ alkoxysilanes (a2). In this case, the $C_1$-$C_6$ alkoxysilanes of type (a2) react with themselves.

Presumably, the product prepared by mixing (a1), (a2), and (a3) contains a mixture of all these dimeric and oligomeric silane condensates.

As can be seen from the reaction schemes shown above, the condensation reactions in turn release either $C_1$-$C_6$ alcohols (for example, ethanol and/or methanol) or water, with the amount of $C_1$-$C_6$ alcohols/water released depending on the extent to which the balance of the above reactions is on the side of the condensates.

The extent of the condensation reaction, in turn, is partly determined by the amount of water (a3) initially added. Preferably, the amount of water is such that the condensation is a partial condensation, where "partial condensation" or "partial condensable groups" in this context means that not all the condensable groups of the silanes presented react with each other, so that the resulting organic silicon compound still has on average at least one hydrolysable/condensable group per molecule.

The amounts of $C_1$-$C_6$ alcohols and water released in the condensation reaction are regarded as by-products whose content can be determined analytically and which can be removed from the reaction mixture by various separation methods (for example, distillation). All $C_1$-$C_6$ alcohols and water contained in the preparation are therefore not included in the definition of product (a). Product (a) within the meaning of the present disclosure refers exclusively to the dimeric or oligomeric silane condensate or a mixture of corresponding silane condensates.

When applying the preparation as contemplated herein on the keratin material, the creation of a stable, coherent, and uniform coating is the basic prerequisite for achieving the desired application properties. Intense and long-lasting colorations can be obtained especially if the colorant compounds can be integrated into an appropriately resistant coating. It has been found that it is essential for this purpose to keep the content of $C_1$-$C_6$ alcohols in the composition as contemplated herein as low as possible.

For this reason, there is a requirement that the composition as contemplated herein contains one or more $C_1$-$C_6$ alcohols (b) in a total amount of about 0.001 to about 10.0% by weight.

For the purposes of the present disclosure, $C_1$-$C_6$ alcohols are alcohols having one or more hydroxy groups comprising from 1 to 6 carbon atoms. These alcohols can be linear or branched, saturated or mono- or polyunsaturated. By $C_1$-$C_6$ mono-alcohols are meant the alcohols from the group of methanol, ethanol, n-propanol, isopropanol, 1-butanol, 2-butanol, 1-pentanol, 2-pentanol, 3-pentanol, 1-hexanol, 2-hexanol and 3-hexanol. $C_1$-$C_6$ alcohols with two hydroxyl groups include ethylene glycol, 1,2-propanediol and 1,3-propanediol. For example, a $C_1$-$C_6$ alcohol with three hydroxyl groups is glycerol.

To comply with these weight specifications, on the one hand the $C_1$-$C_6$ alcohols released during the reactions leading to product (a) must be removed as completely as possible from the reaction mixture. Furthermore, no other $C_1$-$C_6$ alcohols may be added in excessive amounts to the preparation as contemplated herein.

With preparations whose total content of $C_1$-$C_6$ alcohols was about 10.0% by weight, dyeing's with sufficiently high color intensity could be obtained when applied to the keratin material.

However, even better results were obtained when the total content of $C_1$-$C_6$ alcohols—based on the total weight of the composition—could be limited to a total amount of from about 0.01 to about 9.0% by weight, preferably from about 0.1 to about 8.0% by weight, more preferably from about 0.5 to about 7.0% by weight and most preferably from about 0.5 to about 4.0% by weight.

In a further embodiment, very particularly preferred is a composition comprising, based on the total weight of the composition—
 (b) one or more $C_1$-$C_6$ alcohols in a total amount of from about 0.01 to about 9.0% by weight, preferably from about 0.1 to about 8.0% by weight, more preferably from about 0.5 to about 7.0% by weight, and most preferably from about 0.5 to about 5.0% by weight.

Here, the determination or measurement of the content of $C_1$-$C_6$ alcohols is preferably carried out within about 48 hours and very preferably within about 24 hours after the preparation of the formulation, i.e., within about 48 or about 24 hours, respectively, after the product (a) has been obtained by mixing the three components (a1), (a2) and (a3).

In other words, particularly preferred is a composition containing—based on the total weight of the composition—
 (b) one or more $C_1$-$C_6$ alcohols in a total amount of from about 0.01 to about 10.0% by weight, preferably from about 0.01 to about 9.0% by weight, more preferably from about 0.1 to about 8.0% by weight, still more preferably from about 0.5 to about 7.0% by weight, and most preferably from about 0.5 to about 5.0% by weight, wherein the determination of the content of $C_1$-$C_6$ alcohols is carried out within 24 hours after obtaining the product (a) by mixing the three components (a1), (a2) and (a3).

The determination of the content of $C_1$-$C_6$ alcohols in the preparation as contemplated herein can be carried out by employing various analytical methods. One possibility is the measurement using GC-MS. Gas chromatography with mass spectrometry coupling is the coupling of a gas chromatograph (GC) with a mass spectrometer (MS). The overall procedure and/or the instrument coupling is also abbreviated to GC-MS, GC/MS or GCMS.

To determine the content of $C_1$-$C_6$ alcohols, a sample of the preparation can be analyzed by gas chromatography in a double determination on a non-polar column, for example. Identification of the assigned components can be performed by mass spectrometry using library comparison spectra (e.g., NIST® or Wiley®). The mean value is formed from each of the double determinations. Quantification can be performed, for example, by employing internal standard calibration (e.g., with methyl isobutyl ketone).

As already described, $C_1$-$C_6$ alkoxysilanes (a1) and (a2) bearing methoxysilane or ethoxysilane groups are very preferably used in the process as contemplated herein. These have the advantage that methanol and ethanol are released during hydrolysis and condensation, respectively, which can be easily removed from the reaction mixture by vacuum distillation due to their boiling points.

Particularly preferably, the methanol content (b1) is reduced as much as possible in the composition as contemplated herein. A particularly good and resistant coating could be obtained if the composition contained—based on its total weight—from about 0.01 to about 9.0% by weight, preferably from about 0.01 to about 8.0% by weight, more preferably from about 0.01 to about 7.0% by weight and most preferably from about 0.01 to about 4.0% by weight of methanol (1701).

In a further embodiment, very particularly preferred is a composition comprising, based on the total weight of the composition—
(b1) from about 0.01 to about 9.0% by weight, preferably from about 0.01 to about 8.0% by weight, more preferably from about 0.01 to about 7.0% by weight and most preferably from about 0.01 to about 4.0% by weight of methanol.

The measurement of the methanol content in the composition as contemplated herein is preferably carried out within about 48 hours and very preferably within about 24 hours after preparation of the preparation, i.e., within about 48 and about 24 hours, respectively, after obtaining the product (a) by mixing the three components (a1), (a2) and (a3).

In other words, particularly preferred is a composition containing—based on the total weight of the composition—
(b1) from about 0.01 to about 9.0% by weight, preferably from about 0.01 to about 8.0% by weight, more preferably from about 0.01 to about 7.0% by weight and most preferably from about 0.01 to about 4.0% by weight of methanol, the determination of the methanol content being carried out within about 24 hours of obtaining the product (a) by mixing the three constituents (a1), (a2) and (a3).

Furthermore, it is also particularly preferred if the ethanol content (a2) in the composition as contemplated herein is within certain value ranges. A particularly good and resistant coating could be obtained if the composition contained—based on its total weight—from about 0.01 to about 9.0% by weight, preferably from about 0.1 to about 8.0% by weight, more preferably from about 0.5 to about 7.0% by weight and most preferably from about 0.5 to about 4.0% by weight of ethanol (b2).

In a further embodiment, very particularly preferred is a composition comprising, based on the total weight of the composition—
(b2) from about 0.01 to about 9.0% by weight, preferably from about 0.1 to about 8.0% by weight, more preferably from about 0.5 to about 7.0% by weight and most preferably from about 0.5 to about 4.0% by weight of ethanol.

The measurement of the ethanol content in the composition as contemplated herein is also preferably carried out within about 48 hours and very preferably within about 24 hours after the preparation of the formulation, i.e., within about 48 and about 24 hours, respectively, after the product (a) has been obtained by mixing the three components (a1), (a2) and (a3).

In other words, particularly preferred is a composition containing—based on the total weight of the composition—
(b2) from about 0.01 to about 9.0% by weight, preferably from about 0.1 to about 8.0% by weight, more preferably from about 0.5 to about 7.0% by weight and most preferably from about 0.5 to about 4.0% by weight of ethanol, the content of ethanol being determined within about 24 hours of obtaining product (a) by mixing the three constituents (a1), (a2) and (a3).

Compliance with the maximum amounts of $C_1$-$C_6$ alcohols described above can be achieved, for example, by removing the $C_1$-$C_6$ alcohols from the reaction mixture. A particularly preferred method of removing the $C_1$-$C_6$ alcohols is by distillation.

In this context, it is suspected that excessively hot temperatures above 70° C. shift condensation towards high molecular weight products that are too large to be deposited as a closed and resistant film on the keratin material during subsequent keratin treatment. For this reason, it is preferred to maintain a temperature range of about 20 to about 70° C. when removing the $C_1$-$C_6$ alcohols from the reaction mixture.

It is particularly preferred to maintain a temperature range of about 20 to about 65° C., preferably about 20 to about 60° C., more preferably about 20 to about 55° C., still more preferably about 20 to about 50° C., and most preferably about 20 to about 45° C. during the removal of liberated $C_1$-$C_6$ alcohols from the reaction mixture.

The temperature range given here refers to the temperature to which the reaction mixture must be adjusted while the $C_1$-$C_6$ alkoxy silanes are removed from the reaction mixture. This temperature can also be measured, for example, by a calibrated thermometer protruding into this mixture.

In the removal of the $C_1$-$C_6$ alcohols, the setting of the temperature ranges as contemplated herein and the preferred temperature ranges can be carried out, for example, by heating or cooling the reaction vessel or reactor, for example, by placing the reaction vessel in a heating mantle, or by surrounding the reaction vessel from the outside with a temperature-controlled bath, which can be, for example, a water bath or silicone oil bath.

If the reaction is carried out in a double-walled reactor, a temperature-controlled liquid can also be passed through the space formed by the two walls surrounding the reaction chamber.

To ensure that the released $C_1$-$C_6$ alcohols are removed as completely as possible without exceeding the temperature range essential to the present disclosure, the $C_1$-$C_6$ alcohols are preferably removed under reduced pressure (compared to normal pressure). In this context, it has proved particularly advantageous to distill the $C_1$-$C_6$ alcohols from the reaction mixture using a distillation unit. During this distillation, a pressure of about 10 to about 900 mbar is preferably set, more preferably of about 10 to about 800 mbar, still more preferably of about 10 to about 600 mbar and most preferably of about 10 to about 300 mbar.

Vacuum distillation is a common chemical process for which standard commercially available vacuum pumps and distillation apparatus can be used. The distillation apparatus can be in the form of an attachment on the reaction vessel or reactor.

Following vacuum distillation, the volatile alcohols and, if necessary, distilled water can be condensed and collected as liquid distillate in a receiver. Distillation can optionally be carried out with cooling of the evaporated alcohols/water by employing a cooler. The reduced pressure can be generated by employing common processes known in the prior art, typically with a vacuum pump.

Water Content (c) in the Preparation

As the previously shown reaction schemes indicate, too high a water content can also shift the reaction equilibrium from the side of the silane condensates back to the side of the monomeric silanes. Without being limited to this theory, it is assumed in this context that above all the presence of a sufficiently high amount of oligomeric silane condensates is essential for achieving a uniform and resistant coating on the keratin material, which again is the basic prerequisite for producing dyeing results with sufficiently high intensity.

For this reason, it is essential to the present disclosure to limit the water content in the composition as contemplated herein to a value of about 0.001 to about 10.0% by weight of water (c). With preparations whose water content (c) was about 10.0 wt. %, dyeing's with sufficiently high color intensity could be obtained when applied to the keratin material.

However, even better results were obtained when the composition contained—based on the total weight of the composition—about 0.01 to about 9.0% by weight, preferably about 0.1 to about 7.0% by weight, further preferably about 0.2 to about 5.0% by weight and most preferably about 0.5 to about 3.0% by weight of water (c).

In a further embodiment, very particularly preferred is a composition comprising, based on the total weight of the composition—

(c) about 0.01 to about 9.0% by weight, preferably about 0.1 to about 7.0% by weight, more preferably about 0.2 to about 5.0% by weight and most preferably about 0.5 to about 3.0% by weight water.

The measurement of the water content in the composition as contemplated herein is preferably carried out within about 48 hours and very preferably within about 24 hours after the preparation of the formulation, i.e., within about 48 and about 24 hours, respectively, after obtaining the product (a) by mixing the three components (a1), (a2) and (a3).

In other words, particularly preferred is a composition containing—based on the total weight of the composition—

(c) about 0.01 to about 9.0% by weight, preferably about 0.1 to about 7.0% by weight, further preferably about 0.2 to about 5.0% by weight and most preferably about 0.5 to about 3.0% by weight of water, the determination of the content of water being carried out within about 24 hours of obtaining product (a) by mixing the three constituents (a1), (a2) and (a3).

The determination of the water content in the preparation as contemplated herein can be carried out by employing various known analytical methods. One possibility is measurement by GC-MS. Gas chromatography with mass spectrometry coupling is the coupling of a gas chromatograph (GC) with a mass spectrometer (MS). The overall procedure or instrument coupling is also abbreviated as GC-MS, GC/MS or GCMS. Another possibility is the determination of the water content by employing titration, e.g., Karl-Fischer titration.

Another possibility is the determination of the content of water via quantitative NMR spectra, via quantitative 1H-NMR spectra.

Other Ingredients in the Composition

Optionally, the compositions as contemplated herein may also contain one or more further cosmetic ingredients.

The cosmetic ingredients that may optionally be used in step (3) may be any suitable ingredients to impart further beneficial properties to the product. For example, in step (3) of the process, a solvent, a thickening or film-forming polymer, a surfactant compound selected from the group of nonionic, cationic, anionic, or zwitterionic/amphoteric surfactants, colorant compounds selected from the group of pigments, direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates may be utilized.

The selection of these other substances will be made by the specialist according to the desired properties of the agents. Regarding other optional components and the quantities of these components used, explicit reference is made to the relevant manuals known to the specialist.

In this context, it has proven to be particularly preferred to use a cosmetic ingredient in step (3) which further improves the stability, in particular the storage stability, of the keratin treatment agent. In this context, the addition (3) of one or more cosmetic ingredients selected from the group of hexamethyldisiloxane, octamethyltrisiloxane, decamethyltetrasiloxane, hexamethylcyclotrisiloxane, octamethylcyclotetrasiloxane and/or decamethylcyclopentasiloxane has been shown to be particularly beneficial in terms of increasing the stability of the composition.

In another very particularly preferred embodiment, a method as contemplated herein is exemplified by the (3) Addition of one or more cosmetic ingredients selected from the group of hexamethyldisiloxane, octamethyltrisiloxane, decamethyltetrasiloxane, hexamethylcyclotrisiloxane, octamethylcyclotetrasiloxane and/or decamethylcyclopentasiloxane.

Hexamethyldisiloxane has the CAS number 107-46-0 and can be purchased commercially from Sigma-Aldrich®, for example.

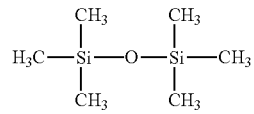

Octamethyltrisiloxane has the CAS number 107-51-7 and is also commercially available from Sigma-Aldrich®.

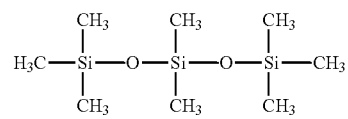

Decamethyltetrasiloxane carries the CAS number 141-62-8 and is also commercially available from Sigma-Aldrich®.

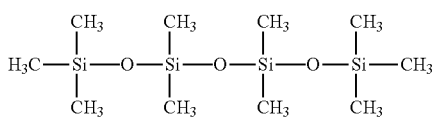

Hexamethylcyclotrisiloxane has the CAS No. 541-05-9.
Octamethylcyclotetrasiloxane has the CAS No. 556-67-2.
Decamethylcyclopentasiloxane has the CAS No. 541-02-6.

To obtain compositions with particularly high storage stability, the addition of a cosmetic ingredient selected from the group of hexamethyldisiloxane, octamethyltrisiloxane, decamethyltetrasiloxane, hexamethylcyclotrisiloxane, octamethylcyclotetrasiloxane and decamethylcyclopentasiloxane has proved to be quite preferred.

In a further very particularly preferred embodiment, the composition as contemplated herein contains
(d) one or more cosmetic ingredients selected from the group of hexamethyldisiloxane, octamethyltrisiloxane, decamethyltetrasiloxane, hexamethylcyclotrisiloxane, octamethylcyclotetrasiloxane and decamethylcyclopentasiloxane.

Explicitly, the use of hexamethyldisiloxane (d) is particularly preferred since compositions with this ingredient have proven to be particularly stable. Preferably, the composition (d) as contemplated herein contains about 10.0 to about 50.0 wt %, preferably about 15.0 to about 45.0 wt %, more preferably about 20.0 to about 40.0 wt %, still more preferably about 25.0 to about 35.0 wt %, and most preferably about 31.0 to about 34.0 wt % hexamethyldisiloxane.

In a further very particularly preferred embodiment, the composition as contemplated herein comprises, based on the total weight of the composition, (d) about 10.0 to about 50.0% by weight, preferably about 15.0 to about 45.0% by weight, more preferably about 20.0 to about 40.0% by weight, still more preferably about 25.0 to about 35.0% by weight, and most preferably about 31.0 to about 34.0% by weight hexamethyldisiloxane.

pH Values of the Preparations

In further experiments, it has been found that the pH of the composition as contemplated herein can also have an influence on the condensation reaction. It was found that alkaline pH values in particular stop condensation at the oligomer stage. The more acidic the reaction mixture, the faster the condensation appears to proceed and the higher the molecular weight of the silane condensates formed during condensation. For this reason, it is preferred if the composition has a pH of from about 7.0 to about 12.0, preferably from about 7.5 to about 11.5, more preferably from about 8.5 to about 11.0, and most preferably from about 9.0 to about 11.0.

The water content of the composition is at most about 10.0% by weight and is preferably set even lower. Particularly in the case of compositions with an exceptionally low water content, measuring the pH with the usual methods known from the prior art (pH value measurement by employing glass electrodes via combination electrodes or via pH indicator paper) can prove difficult. For this reason, the pH values as contemplated herein are those obtained after mixing or diluting the preparation in a 1:1 ratio by weight with distilled water.

Accordingly, the corresponding pH is measured after, for example, about 50 g of the composition as contemplated herein has been mixed with about 50 g of distilled water.

In a further particularly preferred embodiment, a composition as contemplated herein is exemplified in that it has a pH of from about 7.0 to about 12.0, preferably from about 7.5 to about 11.5, more preferably from about 8.5 to about 11.0 and most preferably from about 9.0 to about 11.0, after dilution with distilled water in a weight ratio of about 1:1.

To adjust this alkaline pH, it may be necessary to add an alkalizing agent and/or acidifying agent to the reaction mixture. The pH values for the purposes of the present disclosure are pH values measured at a temperature of about 22° C.

For example, ammonia, alkanolamines and/or basic amino acids can be used as alkalizing agents.

Alkanolamines may be selected from primary amines having a $C_2$-$C_6$ alkyl parent bearing at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

A particularly preferred embodiment is therefore exemplified in that the agent as contemplated herein contains an alkanolamine selected from 2-aminoethan-1-ol and/or 2-amino-2-methylpropan-1-ol as alkalizing agent. Preferred amino acids are amino carboxylic acids, especially α-(alpha)-amino carboxylic acids and w-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, inorganic alkalizing agents can also be used. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Besides the alkalizing agents described above, experts are familiar with common acidifying agents for fine adjustment of the pH-value. As contemplated herein, preferred acidifiers are pleasure acids, such as citric acid, acetic acid, malic acid, or tartaric acid, as well as diluted mineral acids.

Multi-Component Packaging Unit (Kit-of-Parts)

The composition described above is the storage-stable form of the silane blend (i.e., the silane blend), which is as low as possible in $C_1$-$C_6$ alcohols and has a particularly low water content.

For use in a process for the treatment of keratinous material, for the treatment of keratinous fibers, the user must convert this storage-stable blend into an agent ready for use. The ready-to-use agent usually has a higher water content.

For this purpose, the user may mix the previously described low-water composition (i.e., the blend of silane condensates) with one or more other compositions shortly before use. To increase user convenience, all required compositions can be provided to the user in the form of a multi-component packaging unit (kit-of-parts).

Explicitly, the compositions show particularly good suitability when used in a dyeing process.

When the preparation as contemplated herein is used in a dyeing process, one or more color-imparting compounds may be employed. The colorant compound(s) may, for example, be contained in a separately prepared cosmetic formulation (B).

A second object of the present disclosure is a multi-component packaging unit (kit-of-parts) for dyeing keratinous material, in particular human hair, which separately includes a first packaging unit containing a cosmetic preparation (A) and a second packaging unit containing a cosmetic preparation (B), where the cosmetic preparation (A) is a composition as disclosed in detail in the description of the first subject matter of the present disclosure, and the cosmetic formulation (B) comprises at least one colorant compound selected from the group of pigments and/or direct dyes.

The coloring compound or compounds can preferably be selected from pigments, substantive dyes, oxidation dyes, photochromic dyes and thermochromic dyes, particularly preferably from pigments and/or substantive dyes.

Pigments within the meaning of the present disclosure are coloring compounds which have a solubility in water at 25° C. of less than about 0.5 g/L, preferably less than about 0.1 g/L, even more preferably less than about 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein is exemplified in that it contains (b) at least one coloring compound from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

Colored pearlescent pigments are also particularly preferred colorants from the group of pigments as contemplated herein. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein is exemplified in that it comprises (b) at least one colorant compound from the group of pigments selected from the group of colored metal oxides, metal hydroxides, metal oxide hydrates, silicates, metal sulfides, complex metal cyanides, metal sulfates, bronze pigments and/or from mica- or mica-based colorant compounds coated with at least one metal oxide and/or a metal oxychloride.

In a further preferred embodiment, a composition as contemplated herein is exemplified in that it comprises (b) at least one colorant compound selected from mica- or mica-based pigments reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck®, Ariabel® and Unipure® from Sensient®, Prestige® from Eckart® Cosmetic Colors and Sunshine® from Sunstar®.

Particularly preferred color pigments with the trade name Colorona® are, for example:

Colorona® Copper, Merc®k, MICA, CI 77491 (IRON OXIDES)

Colorona® Passion Orange, Merck®, Mica, CI 77491 (Iron Oxides), Alumina

Colorona® Patina Silver, Merck®, MICA, CI 77499 (IRON OXIDES), CI 77891 (TITANIUM DIOXIDE)

Colorona® RY, Merck®, CI 77891 (TITANIUM DIOXIDE), MICA, CI 75470 (CARMINE)

Colorona® Oriental Beige, Merck®, MICA, CI 77891 (TITANIUM DIOXIDE), CI 77491 (IRON OXIDES)
Colorona® Dark Blue, Merck®, MICA, TITANIUM DIOXIDE, FERRIC FERROCYANIDE
Colorona® Chameleon, Merck®, CI 77491 (IRON OXIDES), MICA
Colorona® Aborigine Amber, Merck®, MICA, CI 77499 (IRON OXIDES), CI 77891 (TITANIUM DIOXIDE)
Colorona® Blackstar Blue, Merck®, CI 77499 (IRON OXIDES), MICA
Colorona® Patagonian Purple, Merck®, MICA, CI 77491 (IRON OXIDES), CI 77891 (TITANIUM DIOXIDE), CI 77510 (FERRIC FERROCYANIDE)
Colorona® Red Brown, Merck®, MICA, CI 77491 (IRON OXIDES), CI 77891 (TITANIUM DIOXIDE)
Colorona® Russet, Merck®, CI 77491 (TITANIUM DIOXIDE), MICA, CI 77891 (IRON OXIDES)
Colorona® Imperial Red, Merck®, MICA, TITANIUM DIOXIDE (CI 77891), D&C RED NO. 30 (CI 73360)
Colorona® Majestic Green, Merck®, CI 77891 (TITANIUM DIOXIDE), MICA, CI 77288 (CHROMIUM OXIDE GREENS)
Colorona® Light Blue, Merck®, MICA, TITANIUM DIOXIDE (CI 77891), FERRIC FERROCYANIDE (CI 77510)
Colorona® Red Gold, Merck®, MICA, CI 77891 (TITANIUM DIOXIDE), CI 77491 (IRON OXIDES)
Colorona® Gold Plus MP 25, Merck®, MICA, TITANIUM DIOXIDE (CI 77891), IRON OXIDES (CI 77491)
Colorona® Carmine Red, Merck®, MICA, TITANIUM DIOXIDE, CARMINE
Colorona® Blackstar Green, Merck®, MICA, CI 77499 (IRON OXIDES)
Colorona® Bordeaux, Merck®, MICA, CI 77491 (IRON OXIDES)
Colorona® Bronze, Merck®, MICA, CI 77491 (IRON OXIDES)
Colorona® Bronze Fine, Merck®, MICA, CI 77491 (IRON OXIDES)
Colorona® Fine Gold MP 20, Merck®, MICA, CI 77891 (TITANIUM DIOXIDE), CI 77491 (IRON OXIDES)
Colorona® Sienna Fine, Merck®, CI 77491 (IRON OXIDES), MICA
Colorona® Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)

Other particularly preferred color pigments with the trade name Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.

In addition, particularly preferred color pigments with the trade name Unipure LC® are for example:
Unipure Red LC® 381 EM, Sensient® CI 77491 (Iron Oxides), Silica
Unipure Black LC® 989 EM, Sensient®, CI 77499 (Iron Oxides), Silica
Unipure Yellow LC® 182 EM, Sensient®, CI 77492 (Iron Oxides), Silica In a further embodiment, the techniques as contemplated herein may also contain (b) one or more coloring compounds from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindido, dioxazine and/or triarylmethane compounds.

Examples of particularly suitable organic pigments are carmine, quinacridone, phthalocyanine, sorghum, blue pigments with the Color Index numbers C1 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent as contemplated herein is exemplified in that it contains (b) at least one colorant compound from the group of organic pigments selected from the group of carmine, quinacridone, phthalocyanine, sorghum, blue pigments with the Color Index numbers C1 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent resistance to light and temperature, the use of the pigments in the techniques as contemplated herein is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size $D_{50}$ of about 1.0 to about 50 µm, preferably about 5.0 to about 45 µm, preferably about 10 to about 40 µm, or about 14 to about 30 µm. The mean particle size $D_{50}$, for example, can be determined using dynamic light scattering (DLS).

The pigment or pigments (b) may be used in an amount of from about 0.001 to about 20% by weight, or from about 0.05 to about 5% by weight, in each case based on the total weight of the agent.

As coloring compounds (b), the techniques as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments. Preferably, the direct dyes within the meaning of the present disclosure have a solubility in water (760 mmHg) at 25° C. of more than about 1.0 g/L. In particular, the direct dyes within the meaning of the present disclosure have a solubility in water (760 mmHg) at 25° C. of more than about 1.5 g/L.

Direct dyes can be divided into anionic, cationic, and nonionic direct dyes.

In a further preferred embodiment, an agent as contemplated herein is exemplified in that it contains as coloring compound (b) at least one anionic, cationic and/or non-ionic direct dye.

In a further preferred embodiment, an agent as contemplated herein is exemplified in that it contains (b) at least one anionic, cationic and/or non-ionic direct dye.

Suitable cationic direct dyes include Basic Blue 7, Basic Blue 26, Basic Violet 2, and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-Bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes within the meaning of the present disclosure have a solubility in water (760 mmHg) at 25° C. of more than about 0.5 g/L and are therefore not to be regarded as pigments. Preferably the acid dyes within the meaning of the present disclosure have a solubility in water (760 mmHg) at 25° C. of more than about 1.0 g/L.

The alkaline earth salts (such as calcium salts and magnesium salts) or aluminum salts of acid dyes often have a lower solubility than the corresponding alkali salts. If the solubility of these salts is below about 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange 11, CI 15510, D&C Orange 4, COLIPA n° C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real Red D, FD&C Red Nr. 2, Food Red 9, Naphthol red S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C$_{53}$, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C$_{063}$), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high-water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20% by weight (25° C.).

Thermochromic dyes can also be used. Thermochromism involves the property of a material to change its color reversibly or irreversibly as a function of temperature. This can be done by changing both the intensity and/or the wavelength maximum.

Finally, it is also possible to use photochromic dyes. Photochromism involves the property of a material to change its color depending reversibly or irreversibly on irradiation with light, especially UV light. This can be done by changing both the intensity and/or the wavelength maximum.

The cosmetic preparation (B) may contain—based on the total weight of the cosmetic preparation (B)—one or more pigments in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

The cosmetic preparation (B) may contain—based on the total weight of the cosmetic preparation (B)—one or more direct dyes in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

In addition to preparations (A) and (B), the multicomponent packaging unit (kit-of-parts) as contemplated herein may also contain one or more further separately prepared preparations, for example a cosmetic preparation (C) containing at least one thickening polymer and/or a cosmetic preparation (D) containing at least one film-forming polymer.

In the context of a further embodiment, very particularly preferred is a multi-component packaging unit (kit-of-parts) comprising
   a third packaging unit containing a cosmetic preparation (C), wherein the cosmetic preparation (C) contains at least one thickening polymer A thickening polymer that can be used includes, for example:
   Vinylpyrrolidone/vinyl ester copolymers, such as those sold under the trademark Luviskol® (BASF®). Luviskol® VA 64 and Luviskol® VA 73, each vinylpyrrolidone/vinyl acetate copolymers, are also preferred nonionic polymers.
   Cellulose ethers, such as hydroxypropyl cellulose, hydroxyethyl cellulose and methyl hydroxypropyl cellulose, such as those sold under the trademarks Culminal® and Benecel® (AQUALON®) and Natrosol® grades (Hercules®).
   Starch and its derivatives, especially starch ethers, for example Structure® XL (National Starch), a multifunctional, salt-tolerant starch;
   Polyvinylpyrrolidones, such as those sold under the name Luviskol® (BASF®).

In the context of a further embodiment, very particularly preferred is a multi-component packaging unit (kit-of-parts) comprising
   a fourth packaging unit containing a cosmetic preparation (D), wherein the cosmetic preparation (D) contains at least one film-forming polymer As a film-forming polymer, at least one anionic polymer is selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides of homopolymers or copolymers of methacrylic acid amides, of copolymers of vinylpyrrolidone, of copolymers of vinyl alcohol, of copolymers of vinyl acetate, of homopolymers or copolymers of ethylene, of homopolymers or copolymers of propylene, of homopolymers or copolymers of styrene, of polyurethanes, of polyesters and/or of polyamides.

Concerning the further preferred embodiments of the multicomponent packaging unit as contemplated herein, mutatis mutandis what has been said about the composition as contemplated herein applies.

Examples

1. Preparation of the Silane Blends
1.1. Preparation of Silane Blend 1 (Comparison)

A reactor with a heatable/coolable outer shell and with a capacity of 10 liters was filled with 4.67 kg of methyltrimethoxysilane (34.283 mol). With stirring, 1.33 kg of (3-aminopropyl)triethoxysilane (6.008 mol) was then added. This mixture was stirred at 30° C. Subsequently, 670 ml of distilled water (37.18 mol) was added dropwise with vigorous stirring while maintaining the temperature of the reaction mixture at 30° C. under external cooling. After completion of the water addition, stirring was continued for another 10 minutes.

| (a1) 3-(Triethoxysilyl)propylamine | molar mass = 221.37 g/mol |
|---|---|
| (a2) Methyltrimethoxysilane | molar mass = 136.22 g/mol |
| (a3) Water | molar mass = 18.02 g/mol |

Molar ratio (a2)/(a1)=34.283 mol/6.008 mol=5.706
Molar ratio (a3)/(a1)=37.189 mol/6.008 mol=6.18
Molar ratio (a3)/(a2)=37.18 mol/34.283=1.08

A vacuum of 700 mbar was then applied, and the reaction mixture was heated to a temperature of 44° C. Once the reaction mixture reached the temperature of 44° C., the ethanol and methanol released during the reaction were distilled off over a period of 40 minutes. The distilled alcohols were collected in a chilled receiver. The reaction mixture was then allowed to cool to room temperature. To the mixture thus obtained, 3.33 kg of hexamethyldisiloxane was then dropped while stirring. It was stirred for 10 minutes. In each case, 100 ml of the silane blend was filled into a bottle with a capacity of 100 ml and screw cap closure with seal. After filling, the bottles were tightly closed. The water content was less than 2.0% by weight.

1.2. Preparation of the Silane Blend (2, Present Disclosure)

A reactor with a heatable/coolable outer shell and with a capacity of 10 liters was filled with 4.67 kg of methyltrimethoxysilane (34.283 mol). With stirring, 1.33 kg of (3-aminopropyl)triethoxysilane (6.008 mol) was then added. This mixture was stirred at 30° C. Subsequently, 670 ml of distilled water (37.18 mol) was added dropwise with vigorous stirring while maintaining the temperature of the reaction mixture at 30° C. under external cooling. After completion of the water addition, stirring was continued for another 10 minutes.

| (a1) | 3-(Triethoxysilyl)propylamine | molar mass = 221.37 g/mol |
|---|---|---|
| (a2) | Methyltrimethoxysilane | molar mass = 136.22 g/mol |
| (a3) | Water | molar mass = 18.02 g/mol |

Molar ratio (a2)/(a1)=34.283 mol/6.008 mol=5.706
Molar ratio (a3)/(a1)=37.189 mol/6.008 mol=6.18
Molar ratio (a3)/(a2)=37.18 mol/34.283=1.08

A vacuum of 280 mbar was then applied, and the reaction mixture was heated to a temperature of 44° C. Once the reaction mixture reached the temperature of 44° C., the ethanol and methanol released during the reaction were distilled off over a period of 190 minutes. During distillation, the vacuum was lowered to 200 mbar. The distilled alcohols were collected in a chilled receiver. The reaction mixture was then allowed to cool to room temperature. To the mixture thus obtained, 3.33 kg of hexamethyldisiloxane was then dropped while stirring. It was stirred for 10 minutes. In each case, 100 ml of the silane blend was filled into a bottle with a capacity of 100 ml and screw cap closure with seal. After filling, the bottles were tightly closed. The water content was less than 2.0% by weight.

2. Measurement of the Content of $C_1$-$C_6$ Alcohols by GC-MS

Within 24 hours of their bottling, the ethanol and methanol contents of both silane blends were measured by GC-MS spectroscopy. In a duplicate determination, one sample of each silane blend was analyzed by gas chromatography on a nonpolar column. Identification of the assigned components was performed by mass spectrometry using library comparison spectra (NIST®/Wiley®). Quantification was performed using internal standard calibration with methyl isobutyl ketone. The mean value was calculated from each duplicate determination.

|  | Silane blend 1 (comparison) | Silane blend 2 (Present disclosure) |
|---|---|---|
| Methanol (% by weight) | 10.6/11.6 | 2.9/2.5 |
| Ethanol (% by weight) | 4.6/5.3 | 1.5/1.4 |
| Total C1-C6 alcohols content (average) | 16.1 | 4.2 |

3. Coloring

The following colorant was provided (preparation (B)).

| Preparation (B) | |
|---|---|
| Colorona ® Bordeaux, Merck ®, MICA, CI 77491 (IRON OXIDES) | 5.5 g |
| Eco Smooth Satin (Ethylene/ Sodium Acrylate Copolymer 25% solution, Dow ® Chemical Company) | 40.0 |
| Water | Ad 100 g |

From each of the bottles comprising the previously prepared silane blend, 20 g were weighed out (preparation A). The ready-to-use stain was prepared by shaking 20 g of preparation (A) and 100 g of preparation (B), respectively (shaking for 3 minutes). This mixture was then left to stand for 5 minutes.

For the application, one strand of hair (Kerling Euronaturhaar white) was dipped into the ready-to-use dye and left in it for 1 minute. After that, superfluous agent was stripped from each strand of hair. Then each strand of hair was washed with water and dried. Subsequently, the strands were visually evaluated under a daylight lamp. The following results were obtained:

| Silane blend 1 Comparison 20 g | Silane blend 2 Present disclosure 20 g |
|---|---|
| Colorant (B) 100 g Color: burgundy red Color intensity: low Hiding power: medium | Colorant (B) 100 g Color: burgundy red Color intensity: high Hiding power: medium |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for the treatment of keratinous material, comprising:
   (a) a product obtained by mixing
   (a1) one or more organic $C_1$-$C_6$ alkoxy silanes of the formula (I)

   $$H_2N\text{-}L\text{-}Si(OR_1)_3 \qquad (I)$$

where
   L is a linear or branched divalent $C_1$-$C_{20}$ alkylene group,
   $R_1$ represents a $C_1$-$C_6$ alkyl group,
   with
   (a2) one or more organic $C_1$-$C_6$ alkoxy silanes of the formula (II)

   $$R_2\text{—}Si(OR_3)_3 \qquad (II)$$

where
   $R_2$ represents a $C_1$-$C_{12}$ alkyl group, and
   $R_3$ represents a $C_1$-$C_6$ alkyl group, and
   (a3) water,
   wherein the cosmetic composition is produced from the product, and wherein, based on a total weight of the cosmetic composition, the cosmetic composition comprises
   (b) one or more $C_1$-$C_6$ alcohols in a total amount of from about 0.001 to about 10.0% by weight; and
   (c) from about 0.001 to about 10.0% by weight of the water.

2. The composition according to claim 1, wherein:
   (a1) the one or more organic $C_1$-$C_6$ alkoxy silanes of the formula (I) comprises (3-aminopropyl)triethoxysilane; and
   (a2) the one or more organic $C_1$-$C_6$ alkoxy silanes of the formula (II) comprises methyltrimethoxysilane.

3. The composition according to claim 1, wherein:
   (a1) the one or more organic $C_1$-$C_6$ alkoxy silanes of the formula (I) comprises (3-aminopropyl)triethoxysilane; and
   (a2) the one or more organic $C_1$-$C_6$ alkoxy silanes of the formula (II) comprises ethyltriethoxysilane.

4. The composition according to claim 1, wherein:
   (a1) the one or more organic $C_1$-$C_6$ alkoxy silanes of the formula (I) comprises (3-aminopropyl)triethoxysilane; and
   (a2) the one or more organic $C_1$-$C_6$ alkoxy silanes of the formula (II) comprises methyltriethoxysilane.

5. The composition according to claim 1, wherein:
   (a1) the one or more organic $C_1$-$C_6$ alkoxy silanes of the formula (I) comprises (3-aminopropyl)triethoxysilane; and
   (a2) the one or more organic $C_1$-$C_6$ alkoxy silanes of the formula (II) comprises propyltriethoxysilane.

6. The composition according to claim 1, wherein:
   (a1) the one or more organic $C_1$-$C_6$ alkoxy silanes of the formula (I) comprises (3-aminopropyl)triethoxysilane; and
   (a2) the one or more organic $C_1$-$C_6$ alkoxy silanes of the formula (II) comprises hexyltriethoxysilane.

7. The composition according to claim 1, wherein:
   (a1) the one or more organic $C_1$-$C_6$ alkoxy silanes of the formula (I) comprises (3-aminopropyl)triethoxysilane; and
   (a2) the one or more organic $C_1$-$C_6$ alkoxy silanes of the formula (II) comprises octyltriethoxysilane.

8. The composition according to claim 1, wherein:
   the (a1) one or more organic $C_1$-$C_6$ alkoxy silanes and the (a2) one or more organic $C_1$-$C_6$ alkoxy silanes are mixed with one another in a molar ratio (a2)/(a1) of from about 3.0 to about 8.0.

9. The composition according to claim 1, wherein:
   the (a1) one or more organic $C_1$-$C_6$ alkoxy silanes and the (a3) water are mixed with each other in a molar ratio (a3)/(a1) of from about 4.0 to about 9.5.

10. The composition according to claim 1, wherein:
    The (a2) one or more organic $C_1$-$C_6$ alkoxy silanes and the (a3) water are mixed in a molar ratio (a3)/(a2) of from about 0.1 to about 3.5.

11. The composition according to claim 1, comprising, based on the total weight of the composition, the (a) products in a total amount of from about 30.0 to about 85.0% by weight.

12. The composition according to claim 1, comprising—based on the total weight of the composition
    (b) the one or more $C_1$-$C_6$ alcohols in a total amount of from about 0.01 to about 9.0% by weight.

13. The composition according to claim 1, comprising, based on the total weight of the composition, (b1) from about 0.01 to about 9.0% by weight of methanol.

14. The composition according to claim 1, comprising—based on the total weight of the composition
    (c) from about 0.01 to about 9.0% by weight of the water.

15. The composition according to claim 1, comprising
    (d) one or more cosmetic ingredients selected from the group of hexamethyldisiloxane, octamethyltrisiloxane, decamethyltetrasiloxane, hexamethylcyclotrisiloxane, octamethylcyclotetrasiloxane and decamethylcyclopentasiloxane.

16. The composition according to claim 1, comprising, based on the total weight of the composition, (d) from about 10.0 to about 50.0% by weight of hexamethyldisiloxane.

17. The composition according to claim 1, wherein:
    the composition has a pH of from about 7.0 to about 12.0.

18. A multicomponent packaging unit (kit-of-parts) for dyeing keratinous material, comprising:
    a first packaging unit containing a cosmetic preparation (A) and
    a second packaging unit containing a cosmetic preparation (B),
    where
    the cosmetic preparation (A) is a composition according to claim 1, and
    the cosmetic preparation (B) comprises at least one colorant compound selected from the group of pigments and/or direct dyes.

19. The kit-of-parts according to claim 18, comprising:
    a third packaging unit containing a cosmetic preparation (C), wherein the cosmetic preparation (C) comprises at least one thickening polymer.

20. The kit-of-parts according to claim 18, comprising:
    a fourth packaging unit containing a cosmetic preparation (D), wherein the cosmetic preparation (D) comprises at least one film-forming polymer.

* * * * *